United States Patent [19]

Kwun et al.

[11] Patent Number: 4,979,125
[45] Date of Patent: Dec. 18, 1990

[54] NON-DESTRUCTIVE EVALUATION OF ROPES BY USING TRANSVERSE IMPULSE VIBRATIONAL WAVE METHOD

[75] Inventors: Hegeon Kwun; Gary L. Burkhardt, both of San Antonio, Tex.

[73] Assignee: Southwest Research Institute, San Antonio, Tex.

[21] Appl. No.: 512,037

[22] Filed: Apr. 13, 1990

Related U.S. Application Data

[63] Continuation of Ser. No. 122,763, Nov. 19, 1987, abandoned.

[51] Int. Cl.$^5$ ............... G01N 29/04; G06F 15/46
[52] U.S. Cl. ............... 364/507; 364/508; 364/552; 73/600; 73/602
[58] Field of Search ............ 364/507, 508, 552, 469; 73/596, 598, 599, 600, 602, 651, 158; 340/677, 683

[56] References Cited

U.S. PATENT DOCUMENTS

| | | | |
|---|---|---|---|
| 3,024,645 | 3/1962 | Christoph | 73/71.4 |
| 3,382,713 | 5/1968 | Chutter | 73/151 |
| 4,158,962 | 6/1979 | Conoval | 73/143 |
| 4,376,368 | 3/1983 | Wilson | 57/264 |
| 4,408,285 | 10/1983 | Sisson et al. | 364/508 |
| 4,565,099 | 1/1986 | Arnold | 73/862.41 |
| 4,567,764 | 2/1986 | Jamison et al. | 73/600 |
| 4,591,995 | 5/1986 | Schürch | 364/507 |

OTHER PUBLICATIONS

James Williams et al., "Acoustic-Ultrasonic Nondestructive Evaluation of Double Braided Nylon Ropes Using Stress Wave Factor", *Fibre Science & Technology*, 21(1984), pp. 169-180.

Herbert Weischedel, "The Inspection of Wire Ropes in Service: A Critical Review", *Materials Evaluation*, 43 Dec., 1986, pp. 1592-1605.

Primary Examiner—Parshotam S. Lall
Assistant Examiner—Brian M. Mattson
Attorney, Agent, or Firm—Gunn, Lee & Miller

[57] ABSTRACT

A non-destructive method for evaluating ropes, cables, and strands for flaws and tension is shown. The method permits detecting flaws by recognizing certain vibrational wave amplitude and distribution patterns resulting from striking a test subject with a transverse force. Tension on a test subject is calculated by measuring propagation velocity of the vibrational waves through the test subject. An apparatus is provided which produces vibrational waves in a test subject, measures the amplitude and time distribution of the waves, and displays the measurements for analysis.

11 Claims, 3 Drawing Sheets

FIG_3

NON-DESTRUCTIVE EVALUATION OF ROPES BY USING TRANSVERSE IMPULSE VIBRATIONAL WAVE METHOD

This is a continuation of co-pending application Ser. No. 07/122,763, filed on Nov. 19, 1987, now abandoned.

BACKGROUND OF THE INVENTION

1. Field of the Invention

The present invention relates to non-destructive testing of ropes, cables, and metal strands for flaws and tension.

2. Description of the Prior Art

Non-destructive evaluation (NDE) of ropes is known in the art. Some NDE methods are in practice, while other methods have been proposed, but are not yet perfected. As will be shown hereinafter, no NDE method combines the advantageous features of the transverse impulse vibrational wave method disclosed in this application.

In an article by James H. Williams, Jr., John Hainsworth, and Samson S. Lee entitled "Acoustic-Ultrasonic Nondestructive Evaluation of Double Braided Nylon Ropes Using the Stress Wave Factor" which appeared in *Fibre Science and Technology*, 21 (1984), pp. 169-180, experimentation is performed on synthetic ropes with the object of constructing an analytical model wherein ultrasonic wave conductivity (Stress Wave Factor) of a rope is a function of the condition of the rope and the tension on the rope. It is proposed that such a model would enable accurate testing of ropes for flaws by measuring Stress Wave Factors. To data, no Stress Wave Factor model has been proposed having reliable utility for rope testing. The variation in the relationship between Stress Wave Factor, tension, and rope condition among different rope compositions and structures is not yet fully understood.

Even if an adequate model for interpreting Stress Wave Factor test results were found, the utility of Stress Wave Factor testing would not compare favorably with the transverse impulse vibrational method. While the transverse impulse vibrational wave method permits testing the entire length of a rope from a single test site near one of its ends, Stress Wave Factor method tests only a short length of a synthetic rope because synthetic ropes quickly dissipate the energy of the vibrations used in Stress Wave Factor testing.

Electromagnetic NDE are presently the only type of non-visual method which is in current, widespread practice. Electromagnetic NDE methods are discussed in an article by Herbert R. Weischedel entitled "The Inspection of Wire Ropes in Service: A Critical Review" appearing in *Materials Evaluation*, 43, December 1986, pp 1592-1605.

Electromagnetic NDE methods are used for: (1) localized fault detection (L.F.) and (2) loss of metallic cross-sectional area testing (L.M.A.)

Electromagnetic NDE methods are limited to use on ferromagnetic materials, unlike transverse impulse vibrational wave method which may be performed on ferromagnetic or non-ferromagnetic materials as well as synthetic materials.

L.F. testing is based on the principal that broken wires in a wire rope made of ferromagnetic steels distort a magnetic flux passing the point of breakage causing magnetic flux leakage which is detectable in the area surrounding the rope. L.F. testing is conducted by positioning a strong permanent or electromagnet in close proximity to a wire rope to be tested. As the rope passes the magnet, or the magnet is moved along the length of the rope, a magnetic flux is initiated in the length of rope adjacent to the pole interspace of the magnet. Differential sensing coils are positioned around the rope to detect magnetic flux leakage.

Only major flaws, such as broken wires and severe corrosion pitting, are detected by L.F. testing, because only substantial changes in the magnetic flux leakage are detected by the differential sensors. Small flaws, or widely dispersed flaws, do not produce substantial and rapid magnetic flux leakage changes and are often missed using L.F. testing.

L.M.A. testing involves direct measurement of magnetic flux through a length of a wire rope. Variation in the magnetic flux through different portions of a single rope indicate a change in the cross-sectional area of the rope, which, in turn, indicates possible deterioration of the rope at areas of decreased cross-sectional area.

The electromagnetic methods require passing the entire length of a metallic rope to be tested through the testing apparatus or the testing apparatus be moved along the entire length of the rope. As with Stress Wave Factor testing, the necessity for access to the entire length of a rope reduces the utility of electromagnetic NDE methods.

Methods based on measuring vibrational frequencies of ropes and cables for determining tension are also known in the art. U.S. Pat. No. 4,565,099 issued to Arnold, U.S. Pat. No. 4,376,368 issued to Wilson, and U.S. Pat. No. 4,158,962 issued to Conoval each related to calculating the tension on a rope or cable as a function of its fundamental frequency of vibration. The equipment and methods shown in these patents and otherwise known in the art are not, however, suitable for practicing the non-tension related aspects of the transverse impulse vibrational wave method as described herein.

It would, therefore, be advantageous to develop an NDE method having utility for testing ferromagnetic and non-ferromagnetic ropes alike, which would require access to only a limited portion of the rope to be tested, which would detect minor as well as major rope flaws, and which would permit calculating tension on ropes without additional equipment.

SUMMARY OF THE INVENTION

It is an object of the present invention to provide an apparatus and non-destructive evaluation method which apprises a user of flaws in, and tension on, a cable, rope, or metal strand.

It is another object of the present invention to provide an apparatus and non-destructive evaluation method which apprises a user of the relative amplitudes and arrival time of pulsed, transverse, vibrational waves passing through cable, rope, and metal strand.

It is another object of the present invention to provide an apparatus and non-destructive evaluation method by which the location of a flaw in a cable, rope, or metal strand is determined.

It is another object of the present invention to provide an apparatus and non-destructive evaluation method by which the overall flaw population of a tested cable, rope, or metal strand may be determined.

It is another object of the present invention to provide an apparatus and non-destructive evaluation method by which the tension on cable, rope, or metal strand may be measured.

Accordingly, the present invention provides an apparatus and method utilizing pulsed, transverse, vibrational waves for non-destructive evaluation of cables, ropes, and metal strands for flaws and for tension. The method is referred to as transverse impulse vibrational wave method.

The apparatus for transverse impulse vibrational wave method is designed for initiating a transverse vibrational wave motion in a rope, and for measuring the amplitude of and time intervals between the resulting waves as they travel though the rope. The apparatus comprises an exciting mechanism which applies a transverse impulsive force to the tested rope, a sensor which detects individual waves as they pass a particular point on the rope, a signal amplifier which raises the amplitude of the electrical signals form the sensor, a signal conditioner which filters unwanted signals from the sensor, and an oscilloscope which displays the measurements of the sensor in time versus amplitude units.

The apparatus optionally includes a computer and recorder or graphics printer. The computer is for automating the measurements and calculations involved in detecting and locating flaws in a tested rope, as well as in determining the tension on a tested rope. The recorder and graphics printer are for recording and producing a permanent record of the time/amplitude relationships of the vibrational waves as detected by the sensor.

The transverse impulse vibrational method for NDE of ropes is based on the fact that flaws in a rope partially reflect vibrational wave energy because of the acoustic impedance mismatches at the flaw locations. The wave is also reflected at the ends (or terminations) of the rope. The sensor of the above-described testing apparatus produces corresponding electrical signals.

Calculations based on measurements of the time between the flaw signals and the end-reflected signals and on measurements of the relative amplitudes of the signals detected by the testing apparatus allow the user to locate rope flaws, to determine tension on the tested rope, and to measure the relative population of flaws in the tested rope as compared to a control rope sample.

DETAILED DESCRIPTION OF THE PREFERRED EMBODIMENT

The present invention comprises a method and apparatus for non-destructive evaluation (NDE) of cables, synthetic ropes, and wire ropes for tension and flaws. The method will be referred to as "transverse impulse vibrational wave method" herein. For the purposes of this discussion, cable, synthetic rope, or wire rope will be referred to collectively as "rope" in most instances.

Figure 1:
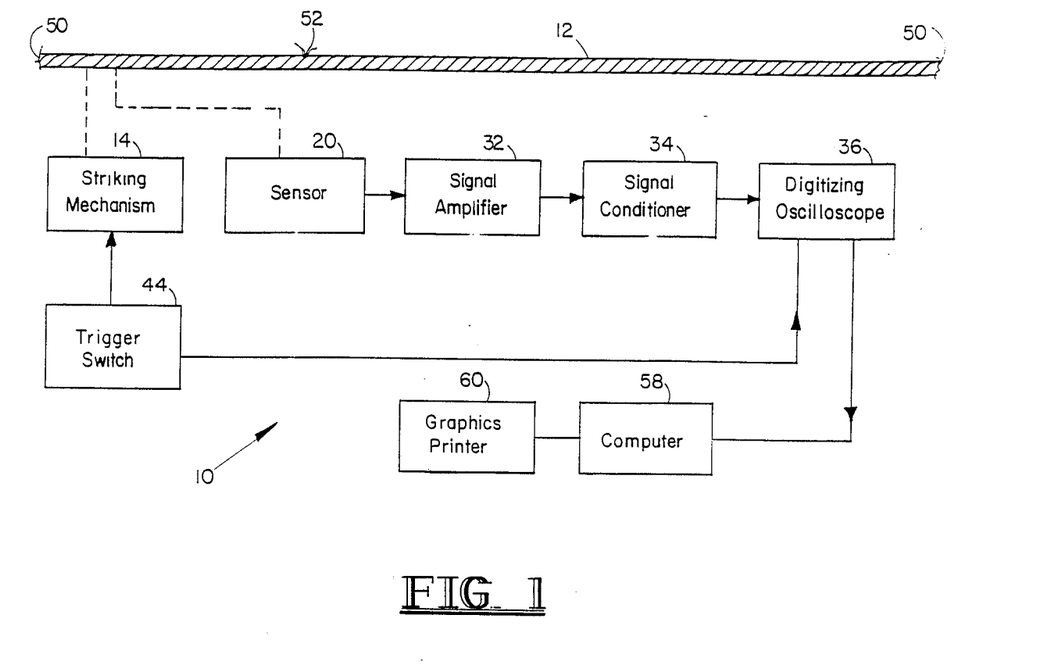
FIG. 1 is a schematic depiction of the testing apparatus for transverse impulse vibrational wave method along with a rope for testing.

Referring to FIG. 1, the testing apparatus is depicted schematically and is referred to generally by the reference numeral 10. For reasons to be discussed hereinafter, the testing apparatus 10 is for detecting individual vibrational waves in a rope 12 and apprising a user of the presence, the relative amplitudes, and the sequential arrangement of the waves.

Figure 2:
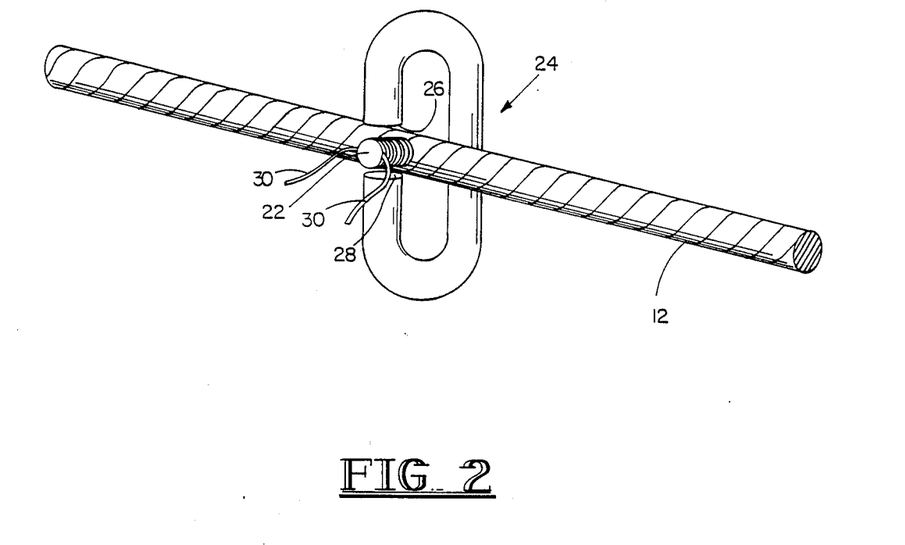
FIG. 2 shows a magnet/coil combination sensor.
Figure 3:
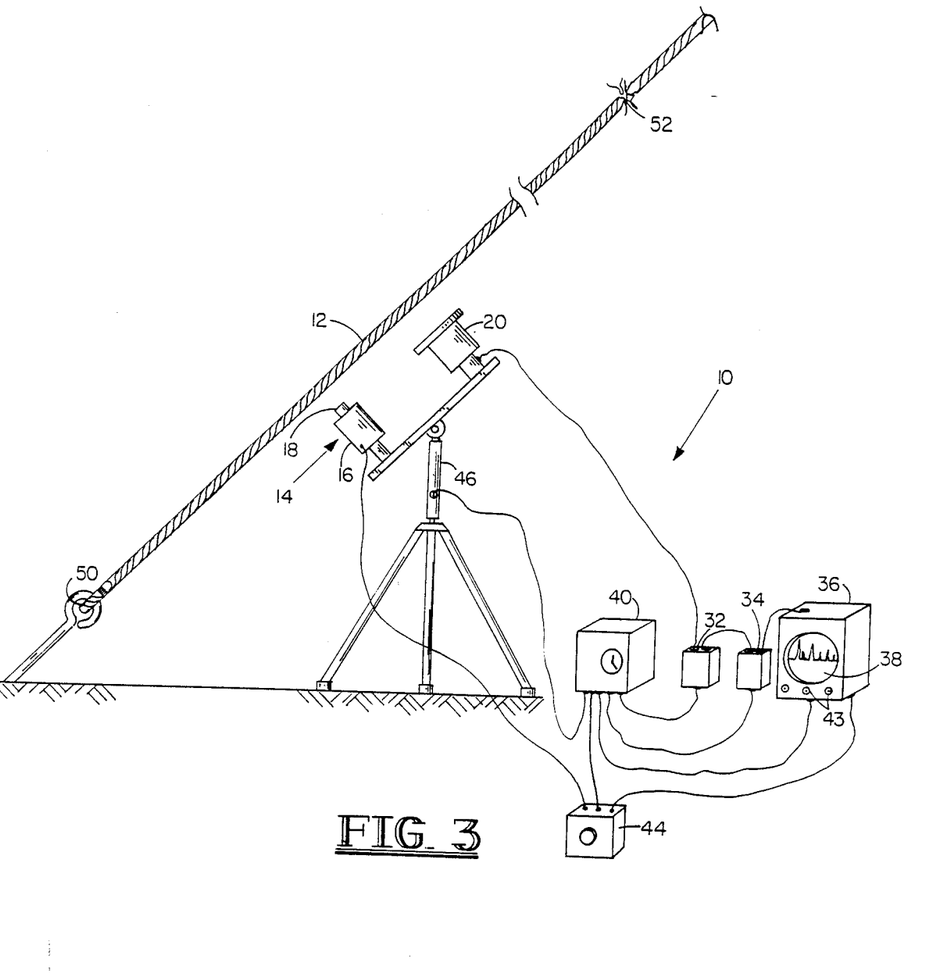
FIG. 3 shows the transverse impulse vibrational wave method testing apparatus set up for field testing a large guy wire.

A rope 12 is shown in FIGS. 1, 2 and 3 to show the relationship of the components of the testing apparatus 10 to a rope 12 which is to be tested.

Transverse Impulse Vibrational (TIV) wave method involves striking a rope 12 to propagate vibrational waves through the rope 12. Consistency in the force used to strike the rope 12 is desirable from one test to another. Consistency of striking force permits direct analytical comparisons to be made between data derived from tests of the same rope at different points in service life of the rope 12 service life or from tests of different ropes. Therefore, the testing apparatus 10 includes a striking mechanism 14 which consistently strikes the rope 12 with a predetermined force. The striking mechanism 14 of the preferred embodiment is a solenoid 16 with its plunger 18 in a position for striking the rope 12 when the solenoid 16 is activated (see FIG. 3). Other designs for striking mechanism 14, such as pneumatic devices or spring biased devices (not shown), would be equally acceptable.

It is noted that although any manner of striking the rope 12 is acceptable for any given test; a device providing consistent striking force is merely desirable for the above-stated reasons. One could, for instance, successfully conduct a TIV wave method test by striking the rope 12 with a hammer (not shown).

Referring again to FIG. 1, a sensor 20 is included in the testing apparatus 10 for detecting individual vibrational waves in the rope 12 resulting from the impact from the striking mechanism 14. To permit testing of a wide range of sizes and compositions of ropes, cables, and strands, the sensor 20 should be capable of discerning individual vibrational waves ranging in frequency up to approximately 1 KHz.

The particular method of detection for the sensor 20 is not important so long as the relative amplitudes and sequential arrangement of vibrational waves in the rope 12 may be derived from the output of the sensor 20. The sensor 20 may measure the actual displacement of the rope 12, velocity of displacement, or acceleration of displacement.

Referring to FIG. 2, one type of sensor 20 which has been used for a TIV wave method comprises a coil 22 and permanent magnet 24 combination. Coil 22 is attached to the rope 12, and is placed between the positive pole 26 and the negative pole 28 of the magnet 24. The leads 30 of the coil 22 are attached to the components of the testing apparatus 10 which process the output of the sensor 20. As the rope 12 vibrates, it causes the attached coil 22 to move relative to the field of the magnet 24. The relative motion of the coil 22 within the magnetic field created by magnet 24, induces a current to flow within the coil 22. This current flow is in direct proportion to the magnitude of the relative motion of coil 22 within the magnetic field which is in turn directly related to the magnitude of the vibrational wave within the rope 12. The induced current flow within coil 22 thereby provides the necessary electrical signal to be processed and analyzed by the remaining components of the testing apparatus 10. Any other available electromagnetic displacement sensor such as the Electro-Mike Displacement Transducer manufactured by the Electro Corp. of Sarasota, Fla., would likewise be appropriate.

Other designs for the sensor 20 are equally acceptable. Devices which physically contact the rope 12 or which detect vibrations by optical methods are examples. An optical sensor 20 such as a laser vibration sensor is shown in FIG. 3. An optical sensor 20 has the advantage of not requiring any direct attachment to rope 12. Light may be directed at the vibrating rope 12 from a distance and may likewise be detected at a distance as shown in FIG. 3. Any available optical device capable of quantitatively detecting the vibrations of the rope 12, such as the Laser Through Beam Photoelectric Sensor, LX Series, manufactured by the Keyence Company, Ltd. of North America, would likewise be appropriate.

Referring to FIG. 1, the testing apparatus 10 includes a signal amplifier 32 which is connected to the sensor 20. The signal amplifier 32 receives the electrical signals from the sensor 20 and amplifies the signals to a level capable of being detected and processed by the other components of the testing apparatus 10. The amplitudes of the signals produced by the signal amplifier 32 are higher, but directly proportional to the amplitudes of the electrical signals from the sensor 20. The outputs of the signal amplifier 32 are, therefore, proportional to the amplitudes of the actual vibrational waves in the rope 12. The relative amplitudes of the vibrational waves in the rope 12 are important to TIV wave method analysis. The frequency response of the signal amplifier 32 should be at least coextensive with the sensor 20.

The testing apparatus 10 further includes a signal conditioner 34 which is connected to the signal amplifier 32 for receiving the amplified signals. The signal conditioner 34 is a variable filter which filters signal frequencies from the signal amplifier 32 falling within a user-defined range. This allows a user to filter signals which are not useful for the test being conducted.

Figure 4:
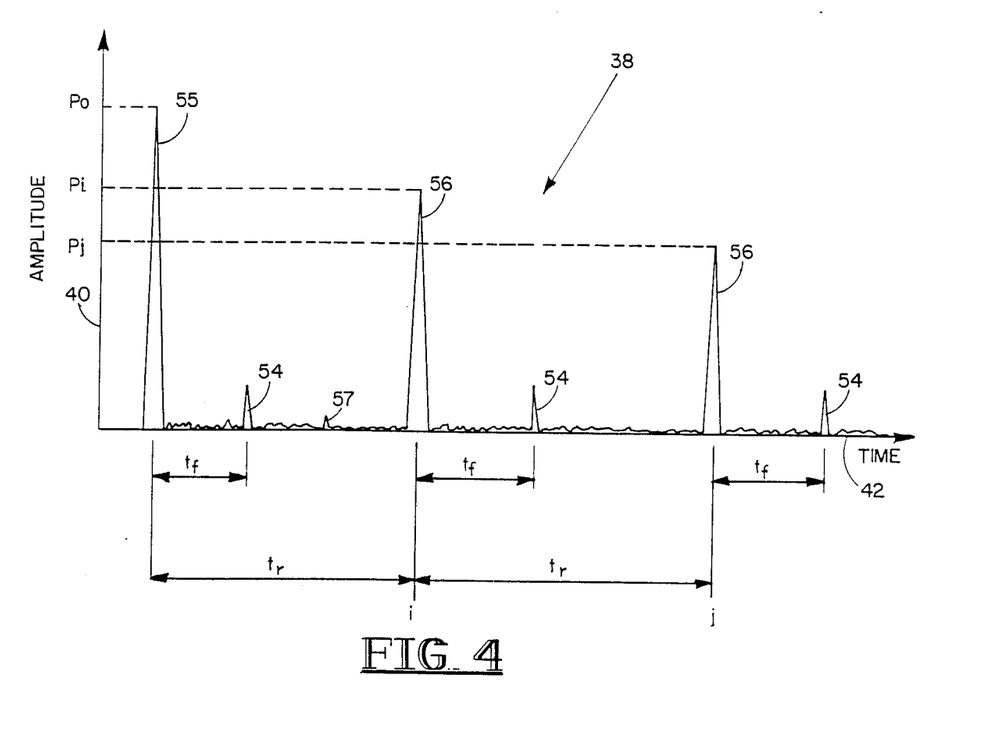
FIG. 4 shows an example of an oscilloscope display obtained by using the transverse impulse vibrational method.

Referring in combination to FIGS. 1 and 4, a digitizing oscilloscope 36 is believed to be the preferred recording/display device for the testing apparatus 10. The oscilloscope 36 is connected to the signal conditioner 34 for receiving the signals from the signal conditioner 34. The display 38 of the oscilloscope 36 has a y-axis scale 40 measured in amplitude units, and an x-axis scale 42 measured in time units. The oscilloscope 36 has calibration controls 43 for adjusting the display 38 to units appropriate to the particular rope 12 being tested.

The digitizing oscilloscope 36 not only gives a graphical representation of the relative amplitudes and sequential arrangement of the signals from the signal conditioner 34, and consequently those of the actual vibrational waves in the rope 12, but also records the signals for later re-display or computer analysis.

Referring again to FIG. 1, a trigger switch 44 activates the striking mechanism 14 and provides a synchronization signal to start the digitizing oscilloscope 36. Therefore, a user may simply throw the switch 44, and the striking mechanism 14 will strike the rope and the electronic components of the testing apparatus 10 will then process and record the resulting vibrational waves. If a computer 58 is used (to be discussed hereinafter), the computer 58 may be interfaced with the switch 44, and it may activate the components of the testing apparatus 10.

Transverse impulse vibrational wave method may be conducted through analysis of data which may be derived by the testing apparatus 10 as just described. Transverse impulse vibrational wave method is made possible because of the measurable effect that flaws and tension have on the vibrational wave propagation properties of cables, ropes, and strands.

It is important to note that TIV wave methods may be performed on ferromagnetic and non-ferromagnetic metallic materials, as well as non-metallic materials alike. This gives TIV wave method a considerable utilitarian advantage over presently used NDE methods. It is of further importance that a TIV wave method alone permits testing an entire length of a cable, rope, or strand from a single access point at one end. As previously mentioned, other NDE methods require passing the testing apparatus over the entire length of a test subject.

Referring to FIG. 3, a TIV wave method will normally be performed on cables, ropes, or metal strands which are in service as elevator cables, guy wires, or in similar highstress and/or safety intensive applications. To perform a TIV wave method test, the striking mechanism 14 is placed within a specified distance of the rope 12 which is to be tested. Because analysis of the test results are simplified by having the sensor 20 in close proximity to the striking mechanism 14, the striking mechanism 14 and the sensor 20 are mounted on a single support stand 46. The remaining components of the testing apparatus 10 are connected as discussed above. A portable power supply 40 is shown in FIG. 3 for use in areas where electricity for the testing apparatus 10 is not readily available.

The striking mechanism 14 and the sensor 20 should be placed near one end 50 of the rope 12. This simplifies analysis of test results because a wave approaches and then is reflected by the end 50 of the rope 12 closest to the sensor 20. These waves will pass the sensor 20 a very short time apart. Therefore, the two passages appear, and can be treated as a single wave for purposes of a TIV wave method.

For simplicity's sake, the vibrational waves created by the impact of the striking mechanism 14 will be referred to as a single wave in the following discussion.

Referring in combination to FIGS. 1, 3, and 4, when a test is conducted with the testing apparatus 10, the rope 12 is struck by the striking mechanism 14, and a vibrational wave is propagated from the point of impact. As the incident wave reaches an end 50 of the rope 12, it is reflected and travels towards the opposite end 50 where it is again reflected. This cycle continues until the energy in the rope 12 is completely dissipated. A flaw 52 in the rope 12 also reflects vibrational waves, but to a lesser extent than the ends 50 of the rope 12. Therefore, waves reflected by the flaw 52 will have a lesser amplitude than waves reflected by the rope's ends 50. Flaw-reflected waves appear, in time, between end-reflected waves because flaw-reflected waves travel a shorter distance than end-reflected waves.

As discussed above, the sensor 20 will produce an electrical signal in response to each vibrational wave of detectable amplitude which passes it. Each electrical signal will have an amplitude proportional to the amplitude of its respective vibrational wave. Signals from an end-reflected wave will, like the wave itself, have a larger amplitude than signals reflecting flaw-reflected waves. Flaws which are large enough to provide reflected waves of measurable amplitude are referred to as "discrete flaws."

Flaws which are too small to reflect such waves are referred to as "non-discrete flaws" (not shown). While not individually detectable, the presence of non-discrete flaws may be recognized by methods which will be discussed hereinafter.

Referring to FIG. 4, a discrete flaw is indicated in the oscilloscope display 38 as a low amplitude flaw signal 54 intervening higher amplitude end signals 56. When a flaw signal 54 does appear, calculations may be conducted to locate the discrete flaw 52 (shown in FIG. 3) which it represents.

Referring again to FIG. 4, the pulse signal 55 is the wave directly resulting from the impact from the striking mechanism 14, and may be treated as an end signal 56.

The position of each discrete flaw 52, the tension on the rope, and the presence of non-discrete flaws (not shown) are determined by formulae, one or more of which require the following variables which may be derived from the oscilloscope display 38:

$t_r$ = the time interval between adjacent end signals 56.
$t_f$ = the time interval between an end signal 56 and the next subsequent flaw signal 54.
$P_i$ = the amplitude of an end signal 56 at point i.
$P_j$ = the amplitude of an end signal 56 at point j.
$L_{ij}$ = the traveling distance of the wave between the two end signals shown by amplitudes $P_i$ and $P_j$.

$t_r$ and $t_f$ are determined simply by measuring the number of time units between two adjacent end signals 56 as indicated by the x axis scale 42 in the oscilloscope display 38.

$P_i$ and $P_j$ are determined by respectively measuring end signals 56 at points i and j on the display 38 of the oscilloscope 36 by reference to the y-axis 40. The attenuation coefficient formula (to be discusses hereinafter) in which these variables are used requires that $P_i > P_j$.

$L_{ij}$ may be derived by multiplying the length (L) of the rope 12 by twice the number of intervals between successive end signals 56 shown between points $P_i$ and $P_j$ on the display 38.

The following two variables which are required by one or more of the transverse impulse vibrational wave method formulae must be independently determined:

L = the length of the rope being tested.
C = the mass per unit length of the rope being tested.

If the entire length of a rope 12 may be viewed, as in FIG. 3 wherein the rope 12 is used as a guy wire, the length (L) may be determined by triangulation. If triangulation is not possible, the length (L) of the rope 12 must be determined by other means—either by direct measurement, or by reference to blueprints, etc.

The mass per unit length (C) of the rope 12 may be acquired from the manufacturer of the rope 12, or may be determined by analysis of a rope sample (not shown) like the particular rope 12 which is to be tested.

Variables which are derived by the method formulae are as follows:

D = the distance of a flaw from the end 50 of the rope 12 closest to the sensor 20.
v = propagation velocity of vibrational waves through the rope 12.
T = the tensile load on the rope 12.
alpha = the attenuation coefficient of vibrational wave in the rope 12.

The distance (D) of a discrete flaw 52 from the end 50 of the rope 12 nearest the sensor 20 may be nearly approximated according to the following formula:

$$D = L(t_f/t_r)$$

The flaw location aspect of the method permits substantial time savings in locating a known discrete flaw 52 for determining the need for replacement of the rope 12. This is a substantial improvement over existing rope testing methods which require passing the testing apparatus over the entirety of the rope 12 to detect and to locate a flaw 52.

During the time between two successive end signals 56, and consequently between two successive passages of an end reflected vibrational waves, the wave will have travelled the length (L) of the rope 12 twice. Therefore, the propagation velocity (v) of vibrational waves in the rope 12 is determined by the following formula:

$$v = 2L/t_r$$

Propagation velocity (v) is a function of the tension (T) on the rope 12 according to the following formula:

$$v = (T/C)^{\frac{1}{2}}$$

The formula for calculating tensile load (T) when propagation velocity (v) is known becomes:

$$T = Cv^2$$

Since the testing apparatus 10 permits calculating the propagation velocity (v) knowing only the rope's 12 length (L) and the constant "C," this formula of the method permits the very simple determination of the tensile load on a rope 12. Such ease of calculation has obvious practical safety implications.

As briefly alluded to above, transverse impulse vibrational wave method includes steps which, in some instances, provide an indicia of non-discrete flaws (not shown) in the rope 12. This aspect of the method is based upon the fact that the rate at which energy in a vibrating rope 12 is dissipated is directly proportional to the population of flaws in a rope 12.

Flaws, whether discrete or non-discrete, interrupt the propagation of vibrational waves through the rope 12, and energy is thereby dissipated more rapidly than in a rope having fewer or no flaws. The rate of energy dissipation in the rope 12 is shown by an attenuation coefficient (alpha). The attenuation coefficient is calculated by the following formula:

$$\text{alpha} = -20 \log \left( \frac{P_j}{P_i} \right) / L_{ij}$$

If the tested rope 12 shows a higher attenuation coefficient (alpha) than a control rope (not shown) known to be flawless, flaws in the rope 12 are indicated.

As indicated above, the variables necessary for calculating the attenuation coefficient are easily derived from the display 38 of the oscilloscope 36.

While there is no way to distinguish between discrete flaws 52 and non-discrete flaws (not shown) by calculating the attenuation coefficient, there is considerable value in making the calculation. This is particularly so when no discrete flaws 52 are detected. A high variance in the attenuation coefficient of the rope 12 from that of a control rope (not shown) would, in such a case, indicate a high non-discrete flaw (not shown) population. Such a rope should be investigated further.

Even when discrete flaws 52 are detected, an experienced user may be able to recognize that the attenuation coefficient for the rope 12 is not in line with the expected value, in light of the severity, or lack thereof of the known discrete flaws 52. Such a disparity would be an indication of a significant non-discrete flaw population in addition to the known discrete flaws 52.

Referring again to FIGS. 1 and 4, as is apparent from the above discussion, proper analysis of the signals from the sensor 20 requires precise measurements of time intervals between end signals 56 and flaw signals 54 and of the relative amplitudes of adjacent end signals 56. Calculations based upon the measured amplitudes and intervals are also required. Therefore, while not necessary to practice transverse impulse vibrational wave method, a computer 58 for automating measurements and calculations is desirable.

The computer 58 should be programed and equipped for the following tasks:
(1) To receive and store data from the digitizing oscilloscope 36 representing the amplitude of and time intervals between the signals initially produced by the sensor 20;
(2) To derive comparative amplitudes of the signals;
(3) To measure time between adjacent end signals 56, as well as between a flaw signal 54 and an adjacent end signal 56;
(4) To receive input of the length of the rope 12 from the user of the testing apparatus 10;
(5) To receive input of the constant C for the particular rope 12 being tested, which constant, when multiplied by the propagation velocity squared, yields the tension on the rope 12, and to make the calculation;
(6) To divide the time between the flaw signal 54 and the adjacent end signal 56 by the time between adjacent end signals 56 and to multiply the quotient by the length of the rope 12 to calculate the discrete flaw's 52 position on the rope;
(7) To measure a difference in amplitude between two adjacent end signals 56 and calculate the attenuation coefficient for the rope 12; and
(8) Most importantly, to provide the derived information in a useful format.

For producing permanent test records, and particularly for preparing graphical depictions of the measurements of the testing apparatus 10 as shown in FIG. 4, a recorder or graphics printer 60 should be attached to the computer 58.

The testing apparatus 10 and formulae just discussed provide a method of testing cable, synthetic rope, and metal strand which has not been previously known. No presently known testing apparatus or method is applicable to ferromagnetic and non-ferromagnetic materials, while at the same time permitting full-length testing from a single location on a cable, rope, or strand.

The ability to test synthetic ropes made of such materials as nylon and KEVLAR ® will enable the use of these ropes for applications previously reserved to metallic cables because of inadequate testing procedures. The ability to test the full length of a cable, rope, or strand will greatly reduce the time and expense involved in testing such things as elevator cables, antenna guy wires, crane support cables, and the like.

We claim:
1. A non-destructive method for evaluating a rope under tension comprising the steps of:
striking said rope at a single point with a force transverse to its length, said force sufficient to produce an incident vibrational wave in said rope, said incident vibrational wave travelling said length of said rope and producing flaw-reflected waves upon encountering a flaw in said rope and producing end-reflected waves upon encountering an end of said rope;
sensing said flaw-reflected waves and said end-reflected waves in said rope at a single point with sensor means adjacent to said rope, said sensor means producing electrical signals having amplitudes directly proportional to amplitudes of said flaw-reflected waves and said end-reflected waves, said electrical signals having a time distribution directly related to a time distribution of said flaw-reflected waves and said end-reflected waves;
receiving and processing said electrical signals from said sensor means whereby said electrical signals may be depicted graphically by display means in amplitude versus time arrangement;
displaying said amplitude and said time distribution of said electrical signals with said display means, said amplitude and said time distribution of said electrical signals representative of said amplitude and said time distribution of said flaw-reflected waves and said end-reflected waves;
monitoring said display means during and after striking said rope to determine said amplitude and said time distribution of said electrical signals produced by said sensor means; and
detecting a sequential pattern of low amplitude electrical signals caused by said flaw-reflected waves intervening higher amplitude electrical signals caused by said end-reflected waves.

2. The method of claim 1 further comprising the steps of:
measuring an end-to-end time ($t_r$), between a first said end-reflected wave and a next said end-reflected wave;
calculating propagation velocity of said end-reflected waves and said flaw-reflected waves in said rope by a propagation velocity formula $$v = 2L/t_r$$

where v represents said propagation velocity, L represents said length of said rope and $t_r$ represents said end-to-end time;
calculating tension on said rope by a rope tension formula $$T = Cv^2$$

where T represents said tension on said rope, C represents mass per unit length of said rope and v represents said propagation velocity.

3. The method of claim 2 further comprising the steps of:
measuring a flaw-to-end time ($t_f$), between a first said flaw-reflected wave and a next said end-reflected wave; and
calculating a position of a flaw indicated by said flaw-reflected waves by a flaw position formula $$D = L(t_f/t_r)$$

where D represents distance of said flaw from an end of said rope closest to said sensor means, L represents said length of said rope, $t_r$ represents said end-to-end time and $t_f$ represents said flaw-to-end time.

4. The method of claim 3 further comprising the steps of:

measuring amplitude ($P_i$) of a first said end-reflected wave;

measuring amplitude ($P_j$) of a next said end-reflected wave;

measuring distance traveled ($L_{ij}$) by said end-reflected waves during a time interval between said first end-reflected wave and said next end-reflected wave; and calculating an attenuation coefficient for said rope whereby overall flaw population in said rope may be determined by an attenuation coefficient formula $$\text{alpha} = -20 \log (P_j/P_i)/L_{ij}$$

where alpha represents said attenuation coefficient, $P_i$ represents said amplitude of said first end-reflected wave, $P_j$ represents said amplitude of said next end-reflected wave, $L_{ij}$ represents said distance travelled by said end-reflected waves during said time interval between said first end-reflected wave and said next end-reflected wave and log indicates a logarithmic function operation.

5. The method of claim 4 further comprising the step of connecting computing means to said display means, said computing means receiving data representing said amplitude of said flaw-reflected waves and said end-reflected waves and said time distribution of said flaw-reflected waves and said end-reflected waves; said computing means receiving input of said length of said rope and said mass per unit length of said rope; said computing means deriving said $t_r$, said $t_f$, said $P_j$, said $P_i$, and said $L_{ij}$ from said data; said computing means calculating said flaw position by said flaw position formula, said tension on said rope by said tension formula, and said attenuation coefficient by said attenuation coefficient formula.

6. A non-destructive method for evaluating a rope under tension comprising the steps of:

striking said rope at a single point with a force transverse to its length, said force sufficient to produce an incident vibrational wave in said rope, said incident vibrational wave travelling said length of said rope and producing flaw-reflected waves upon encountering a flaw in said rope and producing end-reflected waves upon encountering an end of said rope;

sensing said flaw-reflected waves and said end-reflected waves in said rope at a single point with sensor means adjacent to said rope, said sensor means producing electrical signals having amplitudes directly proportional to amplitudes of said flaw-reflected waves and said end-reflected waves, said electrical signals having a time distribution directly related to a time distribution of said flaw-reflected waves and said end-reflected waves;

receiving and processing said electrical signals from said sensor means whereby said electrical signals may be depicted graphically by display means in amplitude versus time arrangement;

displaying said amplitude and said time distribution of said electrical signals with said display means, said amplitude and said time distribution of said electrical signals representative of said amplitude and said time distribution of said flaw-reflected waves and said end-reflected waves;

monitoring said display means during and after striking said rope to determine said amplitude and said time distribution of said electrical signals produced by said sensor means;

detecting a sequential pattern of low amplitude electrical signals caused by said flaw-reflected waves intervening higher amplitude electrical signals caused by said end-reflected waves;

measuring an end-to-end time ($t_r$) between a first said end-reflected wave and a next said end-reflected wave;

calculating propagation velocity of said end-reflected waves and said flaw-reflected waves in said rope by a propagation velocity formula $$v = 2L/t_r$$

where v represents said propagation velocity, L represents said length of said rope and $t_r$ represents said end-to-end time;

calculating tension on said rope by a rope tension formula $$T = Cv^2$$

where T represents said tension on said rope, C represents mass per unit length of said rope and v represents said propagation velocity;

measuring a flaw-to-end time ($t_f$) between a first said flaw-reflected wave and a next said end-reflected wave;

calculating a position of a flaw indicated by said flaw-reflected waves by a flaw position formula $$D = L(t_f/t_r)$$

where D represents distance of said flaw from an end of said rope closest to said sensor means, L represents said length of said rope, $t_r$ represents said end-to-end time and $t_f$ represents said flaw-to-end time;

measuring amplitude ($P_i$) of a first said end-reflected wave;

measuring amplitude ($P_j$) of a next said end-reflected wave;

measuring distance traveled ($L_{ij}$) by said end-reflected waves during a time interval between said first end-reflected wave and said next end-reflected wave; and calculating an attenuation coefficient for said rope whereby overall flaw population in said rope may be determined by an attenuation coefficient formula $$\text{alpha} = -20 \log (P_j/P_i)/L_{ij}$$

where alpha represents said attenuation coefficient, $P_i$ represents said amplitude of said first end-reflected wave, $P_j$ represents said amplitude of said next end-reflected wave, $L_{ij}$ represents said distance travelled by said end-reflected waves during said time interval between said first end-reflected wave and said next end-reflected wave and log indicates a logarithmic function operation.

7. The method of claim 6 further comprising the step of connecting computing means to said display means, said computing means receiving data representing said amplitude of said flaw-reflected waves and said end-reflected waves and said time distribution of said flaw-reflected waves and said end-reflected waves; said computing means receiving input of said length of said rope and said mass per unit length of said rope; said computing means deriving said $t_r$, said $t_f$, said $P_j$, said $P_i$, and said $L_{ij}$ from said data; said computing means calculating said flaw position by said flaw position formula, said tension on said rope by said tension formula, and said attenuation coefficient by said attenuation coefficient formula.

8. An apparatus for testing a rope under tension comprising:

means for striking said rope transversely at a single point to produce an incident vibrational wave along said rope, said incident vibrational wave producing flaw-reflected waves upon encountering a flaw in said rope and producing end-reflected waves upon encountering an end of said rope;

sensor means fixed in a position adjacent said rope for detecting said flaw-reflected waves and said end-reflected waves in said rope at a single point, said sensor means producing an electrical signal having amplitudes and a time distribution proportional to said flaw-reflected waves and said end-reflected waves;

means for amplifying said amplitudes of said electrical signal to detectable and measurable levels; and means for analyzing said electrical signal, said analyzing means detecting and measuring said amplitudes and said time distribution of said electrical signal and discriminating a first portion of said electrical signal indicative of said flaw-reflected waves from a second portion of said electrical signal indicative of said end-reflected waves, so as to locate said flaw.

9. The apparatus for testing a rope as given in claim 8 wherein said analyzing means includes a digitizing oscilloscope for generating a visually perceptible indication of said electrical signal.

10. The apparatus for testing rope as given in claim 9 wherein said analyzing means further includes electronic data processing means, said electronic data processing means receiving output data from said digitizing oscilloscope, said electronic data processing means calculating from said output data a distance from said end of said rope to said flaw.

11. The apparatus for testing a rope as given in claim 8 including between said amplifying means and said analyzing means a signal conditioner to eliminate unwanted noise from said electrical signal.

* * * * *